(12) United States Patent
Lyu et al.

(10) Patent No.: US 10,196,569 B2
(45) Date of Patent: Feb. 5, 2019

(54) METHOD AND SYSTEM OF TREATING BIOMASS WASTES BY BIOCHEMISTRY-THERMOCHEMISTRY MULTI-POINT INTERCONNECTION

(71) Applicant: TONGJI UNIVERSITY, Shanghai (CN)

(72) Inventors: Fan Lyu, Shanghai (CN); Pinjing He, Shanghai (CN); Liming Shao, Shanghai (CN); Hua Zhang, Shanghai (CN)

(73) Assignee: TONGJI UNIVERSITY, Shanghai (CN)

( * ) Notice: Subject to any disclaimer, the term of this patent is extended or adjusted under 35 U.S.C. 154(b) by 245 days.

(21) Appl. No.: 15/168,791

(22) Filed: May 31, 2016

(65) Prior Publication Data
US 2016/0376205 A1 Dec. 29, 2016

Related U.S. Application Data

(63) Continuation of application No. PCT/CN2015/092878, filed on Oct. 27, 2015.

(30) Foreign Application Priority Data

Jun. 29, 2015 (CN) .......................... 2015 1 0366911

(51) Int. Cl.
*C10G 1/00* (2006.01)
*C10B 53/02* (2006.01)
(Continued)

(52) U.S. Cl.
CPC ................ *C10G 1/00* (2013.01); *C05F 11/00* (2013.01); *C05F 17/0027* (2013.01);
(Continued)

(58) Field of Classification Search
CPC .............. C10G 1/00; C10G 2300/1011; C10G 2300/1014; C10G 2300/1018; C10B 53/02; C12P 5/02; C12P 5/023
See application file for complete search history.

(56) References Cited

U.S. PATENT DOCUMENTS

2009/0239279 A1* 9/2009 Hall ......................... C10G 2/32
435/167
2012/0190102 A1* 7/2012 Gitschel ................... C10G 1/10
435/267
(Continued)

FOREIGN PATENT DOCUMENTS

CN 102808000 12/2012
CN 103088073 5/2013
(Continued)

OTHER PUBLICATIONS

Machine translation of CN 104150730, acquired from Google. Mar. 22, 2018.*
(Continued)

*Primary Examiner* — Renee Robinson
(74) *Attorney, Agent, or Firm* — Hamre, Schumann, Mueller & Larson, P.C.

(57) ABSTRACT

The present invention discloses a method and a system of treating biomass wastes by biochemistry-thermochemistry multi-point interconnection. The present invention applies solid, gas and liquid products of the thermochemical treatment subsystem to the biochemical treatment subsystem and applies heat produced by the biochemical treatment subsystem to the thermochemical treatment subsystem, forming multi-point and two-way interconnection between the biochemical treatment subsystem and the thermochemical treatment subsystem, thereby increasing the yield and stability of energy gas of the biochemical treatment subsystem and reducing pollution and energy consumption of the thermo- (Continued)

chemical treatment subsystem respectively. The present invention is suitable for treating biomass wastes with high and low water contents at the same time, producing soil amendment, liquid fuel and biogas, having properties of low secondary pollution and significant reduction of greenhouse gas emission and so on. The bio-stability, humus content and nitrogen content of the solid product are as high as soil amendment, making it easy to store and transport.

5 Claims, 1 Drawing Sheet

(51) Int. Cl.
*C12P 5/02* (2006.01)
*C05F 17/00* (2006.01)
*C05F 11/00* (2006.01)
*C05F 17/02* (2006.01)
*C05G 3/04* (2006.01)
*C09K 17/52* (2006.01)
*C12M 1/00* (2006.01)

(52) U.S. Cl.
CPC ...... *C05F 17/0036* (2013.01); *C05F 17/0045* (2013.01); *C05F 17/0264* (2013.01); *C05G 3/04* (2013.01); *C09K 17/52* (2013.01); *C10B 53/02* (2013.01); *C12P 5/023* (2013.01); *C10G 2300/1011* (2013.01); *C10G 2300/1014* (2013.01); *C10G 2300/1018* (2013.01); *C12M 47/00* (2013.01); *Y02E 50/14* (2013.01); *Y02E 50/343* (2013.01); *Y02P 20/145* (2015.11); *Y02W 30/43* (2015.05); *Y02W 30/47* (2015.05)

(56) References Cited

U.S. PATENT DOCUMENTS

2012/0322130 A1* 12/2012 Garcia-Perez .......... C02F 11/04
435/167
2016/0153008 A1* 6/2016 Josse ....................... C12P 5/023
435/167

FOREIGN PATENT DOCUMENTS

| CN | 103224315 | 7/2013 | |
|---|---|---|---|
| CN | 104031665 | 9/2014 | |
| CN | 104045388 | 9/2014 | |
| CN | 104150730 | 11/2014 | |
| CN | 104958865 | 10/2015 | |
| EP | 2739577 | 6/2014 | |
| WO | WO 2012/109720 | * 8/2012 | ............. C02F 11/04 |
| WO | 2012/166771 | 12/2012 | |

OTHER PUBLICATIONS

Office Action issued in Chinese Patent Application No. CN201510366911.0, dated Jul. 28, 2017, with English translation, 10 pages provided.
International Search Report (English and Chinese) and Written Opinion issued in international application No. PCT/CN2015/092878, dated Mar. 15, 2016, 9 pages provided.
F. Monlau et al., "A new concept for enhancing energy recovery from agricultural residues by coupling anaerobic digestion and pyrolysis process", Applied Energy, 148 (2015) p. 32-38.

* cited by examiner

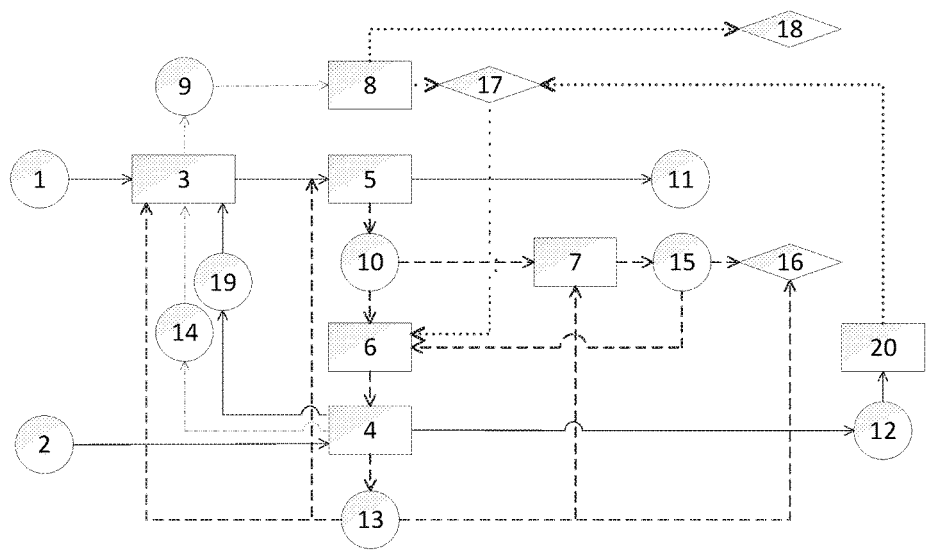

METHOD AND SYSTEM OF TREATING BIOMASS WASTES BY BIOCHEMISTRY-THERMOCHEMISTRY MULTI-POINT INTERCONNECTION

BACKGROUND OF THE INVENTION

Technical Field

The present invention relates to the field of environmental protection and comprehensive utilization of resource, particularly to a method and a system of treating biomass wastes by biochemistry-thermochemistry multi-point interconnection.

Description of Related Art

Biomass wastes include wastes produced by processing and consumption of a variety of biomass, such as the biodegradable part of municipal solid wastes like fruit and vegetable peels from kitchen and food residues, agricultural wastes like livestock manure and crop straws, industrial wastes like slaughterhouse wastes and brewing residues, and municipal sludge, etc. Biomass wastes are an important renewable source. Anaerobic digestion is a traditional biochemical technology to recycle biomass wastes. With anaerobic digestion technology, biomass wastes can be converted into green energy gas-methane, both producing energy source and reducing greenhouse gas emission, and digestion residues (including slurry and fiber digestate) containing nutrients such as nitrogen phosphorus and humus needed by plants can be used as fertilizer or soil ameliorant. As a matter of fact, however, treating biomass wastes with anaerobic digestion technology has a benefit much lower than expected, lying in: 1) organic acids and ammonia of high concentration are produced when easily biodegradable wastes (e.g., fruit and vegetable peels from kitchen, livestock manure) are being degraded. These metabolites inhibit the anaerobic digestion process when accumulated in the anaerobic digestion reactor, resulting in less efficient, unstable, or even failed anaerobic digestion, which needs a very long time to recover. 2) The anaerobic degrading rate of recalcitrantly biodegradable wastes (e.g., crop straws and ground litter with abundant lignocellulose) is relatively slow because of their high content of lignin and cellulose, and they need to be retained in the anaerobic reactor for a very long time. 3) Residues of anaerobic digestion need to be separated into slurry and fiber digestate by solid-liquid separation before further use. However, the solid-liquid separation is not efficient, wherein the solid content of the fiber digestate is only about 8%-25%, while the solid content of the slurry is often 3%-5%. This means if the slurry is drained to the municipal sewer system rather than applied to land directly, it needs to be further treated, and the treating cost of the slurry is quite high. 4) There are a large amount of degradable organic substances left in the fiber digestate due to uncompleted anaerobic digestion, making the digestate unstable, perishable, easy to turn rancid and have leachate, which needs to be further composted before land application. 5) A traditional way to use slurry and fiber digestate is applying them to earth, but, as organic fertilizer, their efficiency is not significant than chemical fertilizers in short term. Thus, they are much less competitive than the chemical fertilizers in the market. Moreover, the application of fertilizer is influenced by the planting season of crops, so a large space is needed to store slurry and fiber digestate. Particularly for biomass wastes produced in urban areas, slurry and fiber digestate produced after anaerobic digestion have to be transferred to places like suburb and countryside by long-distance transportation, which largely increases the cost and difficulty of transportation. Therefore, for sustainable development and promotion of biomass waste anaerobic digestion technology, it is desired to increase the efficiency and stability of the anaerobic digestion process, and to improve the dewatering performance, biochemical stability, storability, transportability and the like of the digestate.

Existing biochemistry-thermochemistry combined technology has only single-point and one-way connection, for example, adding charcoal (a kind of biochar) into an anaerobic digestion reactor according to a Chinese invention patent "Method using charcoal for promoting anaerobic digestion of sludge to produce methane" (Application number: 201310175120.0). Charcoal is added during the composting process as described in a Chinese invention patent "Use of charcoal as exogenous conditioning agent in sludge composting" (Application number: 201310077278.4). As described in a document "A new concept for enhancing energy recovery from agricultural residues by coupling anaerobic digestion and pyrolysis process" (F. Monlau et. al, Applied Energy, 148 (2015) 32-38), heat produced by methane of an anaerobic digestion unit is used for drying fiber digestates, and the dried digestates are used as the feed of a pyrolyzing unit.

BRIEF SUMMARY OF THE INVENTION

To solve the above problems all at once, the present invention provides a method and a system of treating biomass wastes by biochemistry-thermochemistry multi-point interconnection. The present invention is an integrated process, which combines the traditional biochemical technology of anaerobic digestion and thermochemical technology. The thermochemical technology here means pyrolysis, i.e., heating organic substances in an oxygen-free reducing atmosphere to break polymer bonding of the organic substances and break them down into low-molecular-weight substances, and the products of this reaction are gas (pyrolysis gas), oil and coke (biochar), as well as aqueous condensate which is formed by the pyrolysis gas after cooling and treatment. Depending on pyrolyzing conditions, the production rates of the three products of different phases are generally in the range of: pyrolysis gas 7-40% wt, oil 40-70% wt and biochar 8-35% wt.

The object of the present invention can be achieved by the following technical solutions:

a method of treating biomass wastes by biochemistry-thermochemistry multi-point interconnection, characterized in that, includes steps of:

(1) converting dry biomass wastes into pyrolysis gas, biochar, pyrolysis oil and aqueous condensate by a pyrolyzing unit;

(2) feeding the pyrolysis gas and the aqueous condensate into an anaerobic digestion unit for treating wet biomass wastes, wherein carbon monoxide in the pyrolysis gas is converted into methane by carboxydotrophic bacteria and methanogens, hydrogen in the pyrolysis gas is converted into methane by hydrotrophic methanogens, methane and other alkanes increases the high heating value of the pyrolysis gas directly, trace pollutants in the pyrolysis gas are removed by degradation, adsorption, absorption and so on, and the aqueous condensate is degraded into methane.

(3) feeding the biochar into the anaerobic digestion unit wherein the biochar are discharged fiber digestate of the anaerobic digestion unit;

(4) separating the digestion residues into slurry and fiber digestate by a solid-liquid separation unit;

(5) conducting post-treatment on the fiber digestate in a composting unit to form a compost product;

(6) employing heat produced by using the pyrolysis oil and biogas to dry the fiber digestate, the compost and other biomass wastes;

(7) feeding the dried biomass wastes into the pyrolyzing unit again. Preferably, in step (4), biochar is further added before the solid-liquid separation unit to further increase the solid-liquid separation efficiency.

Preferably, in step (5), biochar is further added during the treating process of the composting unit to further improve the compost performance.

Preferably, the compost product in step (5) is used as soil amendment.

Further preferably, the compost product in step (5) is mixed with the biochar to be used as soil amendment.

A system of treating biomass wastes by biochemistry-thermochemistry multi-point interconnection, characterized in that, includes:

a heat treatment subsystem: including a pyrolyzing unit for pyrolyzing dry biomass wastes, a drying unit for drying fiber digestate produced by a solid-liquid separation unit, and a fuel utilization unit for converting heat of pyrolysis oil produced by the pyrolyzing unit;

a biochemical treatment subsystem: including an anaerobic digestion unit for performing anaerobic digestion on wet biomass wastes, a solid-liquid separation unit for conducting solid-liquid separation on digestion residues, and a composting unit for composting fiber digestate produced by the solid-liquid separation unit; and a biogas utilization unit for converting heat of biogas produced by the anaerobic digestion unit.

Although pyrolysis is a mature technology for waste treatment, there are problems as follows when it is used for treating biomass wastes: 1) it is not suitable for wastes with high water content, such as dewatering sludge, fruit and vegetable peels from kitchen and livestock manure, or these wastes need to be pre-dried which is an energy-consumption process, making the efficiency-cost ratio degraded. 2) The yield of pyrolysis gas is not stable, and its calorific value is not as high as gasified gas, so it is often used only by burning, which causes secondary pollution, e.g. dioxin. Particularly when some small nonstandard pyrolyzing furnaces are not provided with facilities for controlling secondary pollution of pyrolysis gas or even emit the pyrolysis gas directly, it will cause energy dissipation and air pollution. 3) The aqueous condensate is a kind of liquid pollutant, which needs to be further treated. The present invention combines anaerobic digestion and pyrolysis technology, wherein the pyrolysis gas and the aqueous condensate can be used and purified by the anaerobic digestion unit, increasing methane produced by anaerobic digestion. Furthermore, heat produced by the methane of the anaerobic digestion and heat produced by using the pyrolysis gas can be used for drying biomass wastes with high water content as well as the fiber digestate, and dried materials can be used as the feed of the pyrolysis. The contributions made by the pyrolyzing unit to the biochemical treatment unit are: 1) the pyrolysis gas and the aqueous condensate are converted into methane in the anaerobic digestion reactor, which increases the yield of methane. 2) Adding biochar during the anaerobic digestion process can improve the stability of anaerobic process, increasing the production efficiency of methane and shorten the reaction time. 3) Biochar can also be applied to composting post-treatment of the fiber digestate, which improves the stability of the compost product, shortens composting period, reducing nitrogen loss and accelerating the humification process.

The present invention applies solid, gas and liquid products of the thermochemical treatment subsystem to the biochemical treatment subsystem and applies heat produced by the biochemical treatment subsystem to the thermochemical treatment subsystem, forming multi-point two-way interconnection between the biochemical treatment subsystem and the thermochemical treatment subsystem, thereby increasing the yield and stability of the biochemical treatment subsystem and reducing pollution and energy consumption of the thermochemical treatment subsystem respectively.

The combined process proposed by the present invention achieves multi-point two-way interconnection between the biochemical unit and the thermochemical unit by pyrolysis gas, aqueous condensate, biochar and biological heat, to increase the comprehensive benefit as far as possible. Particularly, the connection approach, which uses the pyrolysis gas and aqueous condensate as auxiliary raw materials of the anaerobic digestion unit to increase the yield of methane and purify the gas, has few been seen in technical reports.

Comparing with the prior art, the present invention has the following advantages and benefits:

1. Recalcitrantly biodegradable biomass wastes are mainly treated by the pyrolyzing unit, avoiding long retention time in the anaerobic digestion unit, thereby shortening the duration time of anaerobic digestion and reducing the volume of the anaerobic digestion reactor.

2. Methane, hydrogen and carbon monoxide in the pyrolysis gas as well as organic substances contained in the aqueous condensate are all converted into methane in the anaerobic digestion biogas, thereby increasing the yield of methane and the heating value of biogas.

3. Trace pollutants in the pyrolysis gas and the aqueous condensate are removed by degradation, adsorption, absorption and so on after passing the anaerobic digestion unit, and thus purification is achieved, thereby saving the costs for purification of the pyrolysis gas and liquid as well as for the control of secondary pollution.

4. Adding biochar into the anaerobic digestion reactor can enhance the enrichment growing of methanogens and the degrading bacteria of pyrogenetic organic acids, thereby improving the stability of the anaerobic process, accelerating the production of methane, shortening lag phase and anaerobic reaction time.

5. Digestion residues containing biochar have a pore structure, which is relatively sparse and therefore a better dewatering performance, which reduces the solid content of slurry, increases the solid content of fiber digestate. The slurry is clean, which can be drained through pipes after simple treatment, thereby largely reducing slurry treating cost and solving the transportation problem of slurry.

6. Fiber digestate containing biochar has a high solid content, and is easier to be dried.

7. Adding biochar during the composting process can increase the stability of the compost product, shorten the composting period, reducing nitrogen loss, accelerate the humification process and increase the humus content of the compost product.

8. Biochar itself is a good soil amendement that can loosen the soil structure. Compost can be used as fertilizer and soil amendment. Therefore, compost containing biochar is of better potential for land application, and is easy to store and transport.

9. Heat produced by using biogas and pyrolysis oil can be used for drying fiber digestate, compost and other biomass wastes, which saves the drying cost and optimizes the overall economic benefit.

BRIEF DESCRIPTION OF THE SEVERAL VIEWS OF THE DRAWINGS

FIG. 1 is a process flow chart of the present invention.

Reference numbers in the drawing are as follows: 1—wet biomass waste; 2—dry biomass waste; 3—anaerobic digestion unit; 4—pyrolyzing unit; 5—solid—liquid separation unit; 6—drying unit; 7—composting unit; 8—biogas utilization unit; 9—biogas; 10—fiber digestate; 11—slurry; 12—pyrolysis oil; 13—biochar; 14—pyrolysis gas; 15—compost; 16—soil amendment; 17—heat; 18—electricity; 19—aqueous condensate; 20—fuel utilization unit.

DETAILED DESCRIPTION OF THE INVENTION

Hereinafter, the present invention will be described in detail with reference to the drawing and an embodiment.

Embodiment

The method of treating biomass wastes by biochemistry-thermochemistry multi-point interconnection employs a process shown in FIG. 1, including the following steps: (1) converting dry biomass waste 2 into pyrolysis gas 14, biochar 13, pyrolysis oil 12 and aqueous condensate 19 by the pyrolyzing unit 4; (2) feeding the pyrolysis gas 14 and the aqueous condensate 19 into a pyrolysis digestion unit 3 for treating wet biomass waste 1; (3) feeding biochar 13 into the anaerobic digestion unit 3, after which the biochar is fed into the solid-liquid separation unit 5 with the digestion residues; (4) separating the digestion residues into slurry 11 and fiber digestate 10 by the solid-liquid separation unit 5, wherein biochar 13 can be further added before the solid-liquid separation unit 5; (5) conducting post-treatment on the fiber digestate 10 in the composting unit 7 to form a compost product 15, which can be used as soil amendment 16; biochar 13 can be further added in the composting unit 7; (6) generating electricity 18 and heat 17 from the biogas 9 produced by the anaerobic digestion unit 3 through the biogas utilization unit 8, generating heat 17 from the pyrolysis oil 12 by the fuel utilization unit 20, wherein heat 17 is used for the drying operation of the drying unit 6; (7) feeding materials dried by the drying unit 6 into the pyrolyzing unit 4 again.

Taking the treatment of agricultural wastes—livestock manure and crop straws as an example, livestock manure contain 0.5 t of dry organic matter, crop straws contain 0.5 t of dry organic matter, and if a single mesophilic 35° C. anaerobic digestion technology is employed, the retention time requires 40 d, the yield of methane is less than 375 m³. If the biochemistry-thermochemistry multi-point interconnection technology of the present invention is employed, livestock manure (containing 0.5 t of dry organic matter) are fed into the anaerobic digestion unit 3, while crop straws (containing 0.5 t of dry organic matter) are fed into the pyrolyzing unit 4, producing 0.15 t of pyrolysis gas 14, 0.15 t of biochar 13 and 0.2 t of pyrolysis oil 12 under the condition of 500° C. pyrolyzing temperature, wherein the pyrolysis gas contains $CO_2$ 20%, $O_2$ 1%, $N_2$ 2%, CO 30%, $H_2$ 22%, $CH_4$ 25% and some trace pollutants. After being treated by the anaerobic digestion unit 3, CO of the pyrolysis gas 14 is converted into 1.61 kmol of $CH_4$ and $H_2$ thereof is converted into 2.92 kmol of $CH_4$, and together with the original 2.34 kmol of $CH_4$ in the pyrolysis gas, there is totally 6.87 kmol of $CH_4$ converted from the pyrolysis gas. Together with 16.74 kmol of $CH_4$ produced from the organic matters of the livestock manure by 20 d of mesophilic 35° C. anaerobic digestion, the total yield of methane is 23.61 kmol, equivalent to 529 m³. Furthermore, the 0.2 t of pyrolysis oil 12 produced by this interconnection technology can be directly used as liquid fuel, and the 0.15 t of biochar 13 is recycled solid product which is easy to transport and store, and can be directly used as soil amendment 16 or as an additive of the anaerobic digestion unit 3, or as a conditioner of the solid-liquid separation unit 5, or as an additive of the composting unit.

The interconnection technology of the present invention also has a good effect of reducing greenhouse gas emission. If the abovementioned livestock manure and crop straws both containing 0.5 t of dry organic matter are open dumped or landfilled randomly, greenhouse gas produced will be 8.4 t of $CO_2$ equivalent. However, if a single anaerobic digestion treatment is employed, methane produced substitutes fossil fuels, and the fiber digestate are landfilled, then greenhouse gas produced is 4.255 t of $CO_2$ equivalent. If a single anaerobic digestion treatment is employed, methane produced substitutes fossil fuels, and the fiber digestate are used as organic fertilizer instead of the chemical fertilizer to achieve organic farming, then the greenhouse gas produced is –0.1175 of $CO_2$ equivalent. If using the interconnection technology of the present invention with a higher yield of methane, and replacing fossil fuels with pyrolysis oil and using fiber digestate containing biochar as organic fertilizer instead of chemical fertilizer to achieve organic farming, then the greenhouse gas produced is –0.998 of $CO_2$ equivalent. The waste treatment can be converted from carbon source technology into carbon sequestration technology.

The above description of embodiments is only for easy understanding and using of the present invention by one of ordinary skill in this art. Those skilled in this art can easily make various changes to these embodiments and apply the general principle described here to other embodiments without creative work. Therefore, the present invention is not limited to the above-described embodiment, and modifications and changes made without departing from the scope of the present invention by those skilled in this art according to the disclosure of the present invention would fall within the scope of the present invention.

What is claimed is:

1. A method of treating biomass wastes by biochemistry-thermochemistry multi-point interconnection, comprising:

(1) converting dry biomass wastes into pyrolysis gas, biochar, pyrolysis oil and aqueous condensate by a pyrolyzer;

(2) feeding the pyrolysis gas and the aqueous condensate into an anaerobic digester to obtain biogas and digestion residues;

(3) feeding at least a portion of the biochar into the anaerobic digester wherein the portion of the biochar is discharged with the digestion residues in the anaerobic digester;

(4) separating the digestion residues into slurry and fiber digestate by a solid-liquid separator;

(5) composting a first portion of the fiber digestate in a composter to form a compost product;

(6) employing heat generated from the pyrolysis oil and the biogas to dry a second portion of the fiber digestate, the compost product and other biomass wastes to obtain dried biomass wastes;

(7) feeding the dried biomass wastes into the pyrolyzer, wherein step (4) further includes adding at least another portion of the biochar before separating the digestion residues to further increase the solid-liquid separation efficiency.

2. The method of treating biomass wastes by biochemistry-thermochemistry multi-point interconnection of claim 1, wherein step (5) further includes adding at least another portion of the biochar into the composter to further improve performance of the composting.

3. The method of treating biomass wastes by biochemistry-thermochemistry multi-point interconnection of claim 1, wherein, in step (2), the pyrolysis gas and the aqueous condensate are converted into the biogas by biochemical actions in the anaerobic digester and trace pollutants contained in the pyrolysis gas are removed, and
the biogas contains methane.

4. The method of treating biomass wastes by biochemistry-thermochemistry multi-point interconnection of claim 1, wherein the compost product in step (5) is used as soil amendment.

5. The method of treating biomass wastes by biochemistry-thermochemistry multi-point interconnection of claim 4, wherein the compost product in step (5) is mixed with the biochar to be used as soil amendment.

\* \* \* \* \*